United States Patent [19]

Muñoz

[11] 4,312,334
[45] Jan. 26, 1982

[54] BRACE FOR THORAX FRACTURES

[76] Inventor: Antonio S. Muñoz, Lázaro de Baigorri 419, Chihuahua, Chih., México

[21] Appl. No.: 61,159

[22] Filed: Jul. 26, 1979

[51] Int. Cl.³ .............................................. A61F 5/02
[52] U.S. Cl. .................................................. 128/78
[58] Field of Search ....................... 128/74, 75, 78, 94, 128/95

[56] References Cited

U.S. PATENT DOCUMENTS

| 810,580 | 1/1906 | Storms | 128/94 |
| 3,095,875 | 7/1963 | Davidson et al. | 128/78 |
| 3,827,429 | 8/1974 | Heikes | 128/78 |

Primary Examiner—Robert W. Michell
Assistant Examiner—T. J. Wallen
Attorney, Agent, or Firm—Ladas & Parry

[57] ABSTRACT

A brace for thorax fractures permitting ambulatory movement of the patient. The brace comprises a rigid square shaped back member with an internal concave face that can be held on a patient's back by adjustable straps under the armpits and across the waistline. This back member carries curved rib members fixed to and extending outwardly from the back member. Fractures or sunken sections of the patient's thorax can be wired to these rib members to maintain them in desired suitable position while osseous callus is formed.

3 Claims, 3 Drawing Figures

BRACE FOR THORAX FRACTURES

BRIEF DESCRIPTION OF THE INVENTION

In general terms this invention refers to a new brace for thorax fractures which allows the controlled traction of the patient's costal fragments, thus avoiding paradoxical breathing and keeping the patient in ambulatory shape. This brace has a rigid member adaptable to the back of the thorax. The rigid member is held in position by means of two belts starting from the upper end of said member to the side end of it, passing under the armpit, and by another belt fixed at the inferior side end of the member to the opposite extreme at the waistline. Also, it is provided with outwardly extending rib members extending from the upper part of the rigid member to the lower end thereof. The ligaments holding the fractured part are fixed to the above mentioned ribbing, so the use of this brace does not require keeping the patient in bed during the therapy period.

BACKGROUND OF THE INVENTION

Thorax injuries caused by accidents, cause paradoxical breathing with air ventilation failures and an increase of the $CO_2$ partial pressure, appearing in four or five days in the traumatic humid lung, causing insufficient breathing and therefore, death; when there are multiple costal fractures with flaccidity on the thorax walls, at the moment of inspiration the affected area sinks, passing the air from this area to other thorax areas, so for this reason there is no ventilation and at the moment of expiration from other unaffected parts of the thorax, the air goes to the multiple fractures underlying areas, so there will always be non-ventilated (saturated $CO_2$) in the fractures underlying areas; for these reasons it is necessary to pull the sunken part and keep it in its position to form the osseous callus, therefore giving a certain rigidity to the fracture.

Multiple side fractures with loss of the thorax rigidity and consequently paradoxical breathing, have been treated in different ways in the past.

Originally, fractured parts were held with pincers and traction was provided with a pulley with a 6 to 8 Kg, counterweight in an orthopedic bed. Later, the fragments were fixed with pericostal or intramedular wire.

This type of apparatus is obviously very unconfortable and the patient must remain in orthopedic bed practically immovable.

Another type of device used to control these fractures is the endotracheal probe to keep the patient breathing with an air flow at a positive/negative pressure until the osseous callus is formed to give some rigidity to the fracture.

The inconvenience of using this system is that the patient should remain in intensive therapy for at least two weeks with an endotracheal probe, which is very unconfortable and costly, because sophisticated and complicated control instruments are required, such as the gasometry control in the patient to keep him breathing adequately, besides, highly specialized personnel is required to use such apparatus.

The advantages of this invention with respect to the above mentioned procedures, are that the patient does not have to remain in bed for several weeks, he does not need endotracheal probes for the supply of air flow since the prosthesis is placed in the patient immediately after surgery, and he can walk with the brace on him without any risk.

The brace for thorax fractures includes a rigid member to be set on the back of the thorax (back of the patient) and held in position by belts extending from the upper end of the rigid member to the sides thereof passing under the armpits, and by another adjustable belt extending between the lower side ends of the rigid member at the waistline. The rigid member is provided with curved rib members extending from the upper end of the rigid member to the lower end thereof: the fragments loosened in the thorax are held to the rib members with wires in order that the controlled traction of the fragments is perfectly achieved, avoiding paradoxical breathing and keeping the patient in ambulatory shape.

This type of fractures generally occur in automobile accidents or in sports accidents like American football, where when receiving a strong blow on some part of the thorax a fracture or a sinking of the flexible thorax areas is caused. It is necessary to unite or pull the fragments to the adequate position and keep them like that until the osseous callus is formed to give a certain rigidity to the fracture. For all this, the brace here described is of great help, since the union of the fragments can be kept in position by fixing them with wires to the rib members of the brace so that it is not necessary for the patient to remain in bed for several weeks.

Another advantage of the invention is that the patient uses his own respiratory muscles and can cough to move and throw out the bronchial secretions.

DETAILED DESCRIPTION OF THE INVENTION

Figure 1:
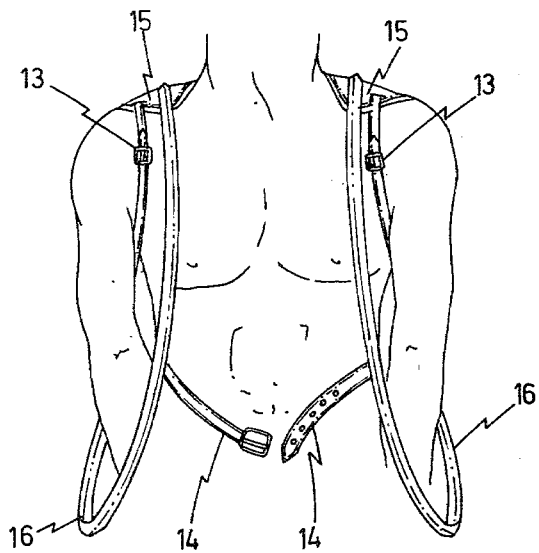
FIG. 1 is a frontal view showing the way to put the brace on the patient with a thorax injury.
Figure 2:
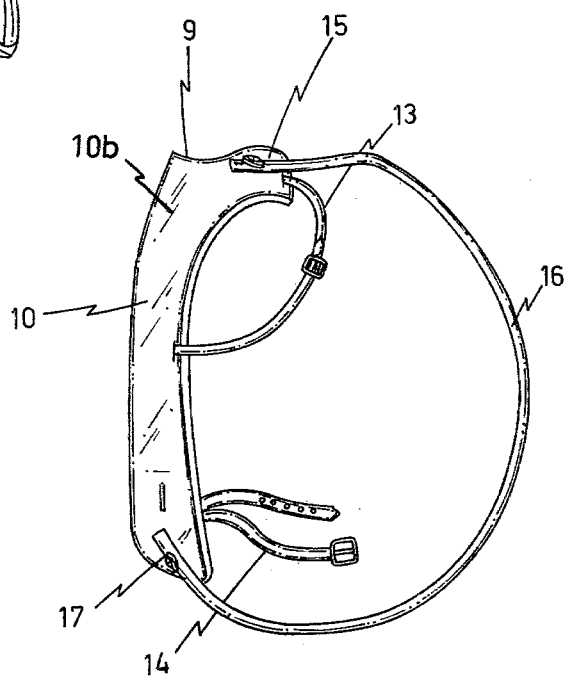
FIG. 2 is a side view of the brace.
Figure 3:
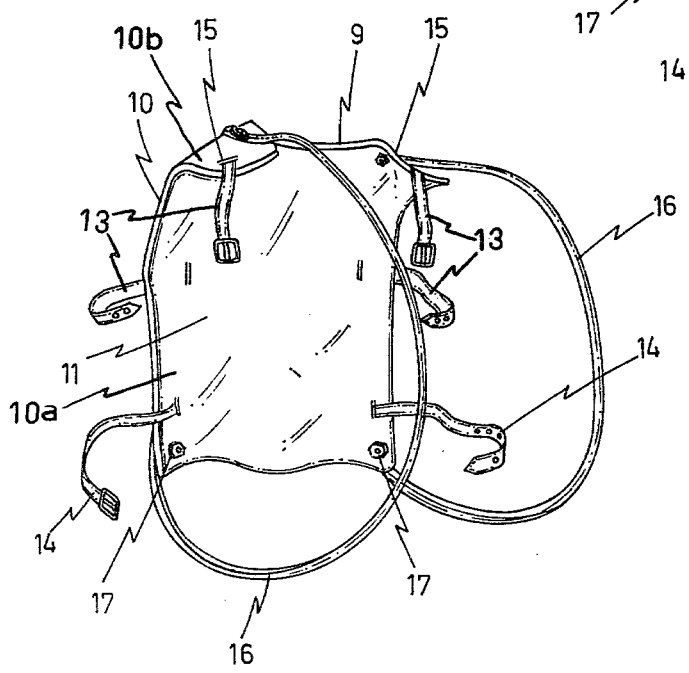
FIG. 3 is a conventional perspective in which all the parts forming the brace can be seen.

The present brace for thorax fractures 9, is formed by a rigid square shaped back member 10, which has inwardly bent upper ends 15 and presents the approximate form of the patient's back. It has an internal concave face 10a, and the corresponding convex external face 10b in the internal concave face 10a of the member 10, there is a padding 11 for the better accomodation to and comfort of the user. Said back member 10 is mounted on the thorax of the patient by two adjustable belts 13, extending between the inwardly bent upper ends 15 of member 10 and intermediate side portions thereof and passing under the patient's armpits, and by another adjustable belt 14 extending between the lower ends of member 10 at the waistline of the patient.

Said member 10 has also curved rib members 16 which extend from the upper ends 15 of said member 10, to the lower back section 17 thereof.

The fractured or sunken section of the thorax is tied up with wire of the type used in this kind of surgery, and traction is provided by the rib members which are fixed to the rigid member with screws or any other type of fixed or removable holder; to these rib members the wire is fastened to hold the fractured or sunken part in a desired suitable position.

The curved rib members 16 may be maintained parallel to each other, or in crossed form as required by the position of the thorax injury, and the length may vary depending on the requirements of the patient.

Notwithstanding that the above description has been made in relation to a specific form of the invention, it should be understood by those experts in this matter that any modification as to the type of brace for thorax or any change to it should be considered within the essential meaning and scope of the present invention.

What I claim is:

1. A brace for thorax fractures which permits ambulatory movement of a patient without need of remaining in an orthopedic bed or in intensive therapy, which comprises a rigid square shaped and curved back member having upper ends bent around the patient's shoulders and an internal concave face corresponding approximately to the shape of a patients back to cover the area between shoulders and waist;

two adjustable belts extending from the upper ends of the back member to sides thereof and adapted to pass under the patient's armpits;

an adjustable belt extending between lower ends of the back member at the patient's waistline;

and curved rib members extending outwardly from the upper ends to the lower ends of the back member and fixed thereto;

whereby fractures or sunken sections of the patient's thorax can be wired to the rib members to maintain them in desired suitable position while osseous callus is formed.

2. A brace according to claim 1 in which the rib members are adapted to be maintained in parallel or crossed positions according to the positional requirements of the thorax injury.

3. A brace according to claim 1 in which the internal concave face of the back member is provided with a layer of padding.

* * * * *